United States Patent [19]

Harris

[11] Patent Number: 5,011,281
[45] Date of Patent: Apr. 30, 1991

[54] HUMIDIFICATION AND CLOUD CHAMBER BLOCK FOR PARTICLE CONCENTRATION DETECTION

[75] Inventor: Eric W. Harris, Moncks Corner, S.C.

[73] Assignee: Research Equipment Corporation, North Charleston, S.C.

[21] Appl. No.: 408,880

[22] Filed: Sep. 18, 1989

Related U.S. Application Data

[63] Continuation-in-part of Ser. No. 352,149, May 15, 1989, Pat. No. 4,967,187.

[51] Int. Cl.⁵ ............................................. G01N 1/00
[52] U.S. Cl. ......................................................... 356/37
[58] Field of Search .......... 73/865.5; 356/37, 437–439; 340/627; 250/335, 573, 574, 576

[56] References Cited

U.S. PATENT DOCUMENTS

| | | | |
|---|---|---|---|
| 3,694,085 | 9/1972 | Rich | 356/37 |
| 3,738,751 | 6/1973 | Rich | 356/37 |
| 4,293,217 | 10/1981 | Bird, Jr. et al. | 356/37 |
| 4,792,199 | 12/1988 | Borden | 356/37 |

*Primary Examiner*—Robert Raevis
*Attorney, Agent, or Firm*—Collard, Roe & Galgano

[57] ABSTRACT

A device consisting of a monolithic block of material that is used as a housing of an apparatus for determining the density, or changes in density, of small particles, that contains an elongated chamber formed within the block that serves as a cloud chamber, and a trough formed in said block and defining a humidification chamber. The block includes passageways that connect the cloud chamber to the humidification chamber and inlet and exhaust passageways, as well as providing mountings for various valves, such as a humidity valve, by-pass valve, and vacuum valve used in the apparatus.

5 Claims, 3 Drawing Sheets

HUMIDIFICATION AND CLOUD CHAMBER BLOCK FOR PARTICLE CONCENTRATION DETECTION

This is a continuation-in-part of application Ser. No. 352,149, filed May 15, 1989 now U.S. Pat. No. 4,967,187. This invention relates to a humidification and cloud chamber block for measuring the concentration of submicron size particles in the air by means of a cloud chamber.

BACKGROUND OF THE INVENTION

In different environments there is always an accumulation of particles of various sizes. By monitoring the concentration of particles within a narrow size range using a cloud chamber, the presence of a fire, even in its earliest stags, within the monitored space may be detected. An air sample from the space being monitored is introduced into the cloud chamber after passing through a humidity chamber.

The humidification of the gas sample and cloud formation is performed with an integrated humidification/cloud chamber assembly. The main component in this assembly is the humidification/cloud chamber block. This block is machined preferably from the plastic Ertalyte, and has several advantages over prior art devices. The block contains all porting and passages between the humidification chamber and cloud chamber, and therefore minimizes connecting passage lengths. Moreover, due to the insulating qualities of Ertalyte, the block minimizes thermal gradients between the humidification chamber and the cloud chamber. This is an advantage over prior art devices since there are no external interconnecting pipes or tubing which require thermal insulation. The reduction in external "plumbing" also reduces the possibility of leaks in the system. The Ertalyte plastic is essentially inert and therefore resists scale buildup in the humidification chamber, an advantage over the aluminium humidification chamber in some prior art designs. The stability of the Ertalyte plastic also allows the cloud chamber to be directly machined in the block. This has an advantage over prior art devices that use a high quality glass or metal tubing liner to provide a stable optical path for cloud detection. This results in more parts, greater expense, and more plumbing connections.

The assembly incorporates computer controlled solenoid valves to control the flow of the fluid sample through the humidification/cloud chamber. Valve timing is readily adjustable by computer software changes to accommodate different sample flow rates, allowing for more flexibility in the selection of vacuum sources. This is an advantage over the fixed, mechanical valve timing utilized in the prior art. A further advantage of using computer controlled solenoid valves in the block assembly is the ability to vary the time between samples. By cycling the system at a slow rate until an increase in the number of condensation nuclei is detected, system water use is minimized. Reduced water use requires a smaller water reservoir, which in turn allows the entire inventive system to be placed in a smaller enclosure.

The monitor uses a microcomputer to control its operation instead of dedicated analog and/or digital circuits of the prior art. Since only a fraction of the microcomputer's capacity is used for the system's operation, complex additional tasks have been assigned to the microcomputer without having to resort to additional complex electrical circuitry. For example, the microcomputer is used to communicate the system's mechanical and electrical status as well as condensation nuclei concentration to any remote location using the EIA RS-232 communications protocol. This has the advantage of being able to transmit a large amount of information over a minimum number of supervised conductors. The microcomputer has the further advantage of continuously storing in memory a running seven day historical record of the condensation nuclei concentration for the area being protected. This produces a record "signature" of the area being protected which may be used to adjust the "alarm", "alert" or "warning" condensation nuclei concentration levels to be more in line with the base concentration levels in the area being protected.

It is therefore an object, according to the present invention, to provide a humidification and cloud chamber block which can be used for measuring the concentration of submicron particles in the air by means of a cloud chamber.

It is another object, according to the present invention, to provide a humidification and cloud chamber block which is simple in design, easy to manufacture and reliable in use.

Other objects and features of the present invention will become apparent from the following detailed description considered in connection with the accompanying drawings which disclose the embodiments of the invention. It is to be understood, however, that the drawings are designed for the purpose of illustration only and not as a definition of the limits of the invention.

In the drawings wherein similar reference characters denote similar elements throughout several views.

Figure 1:
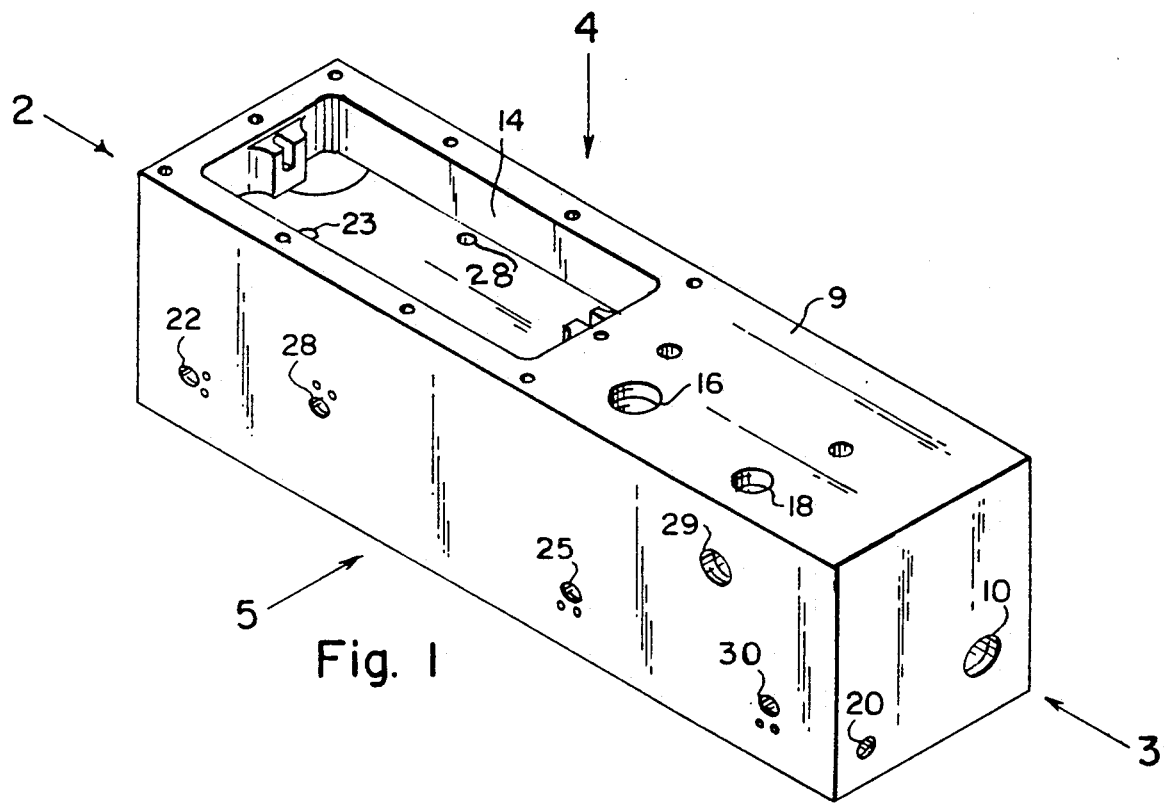
FIG. 1 is a prespective view of the humidification and cloud chamber block according to the invention.
Figure 2:
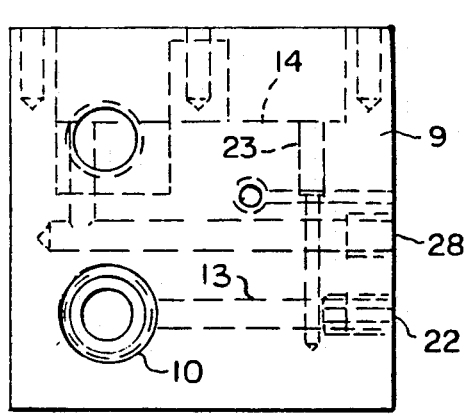
FIG. 2 is an end view taken along section 2 of FIG. 1 and shown partly in cross-section.
Figure 3:
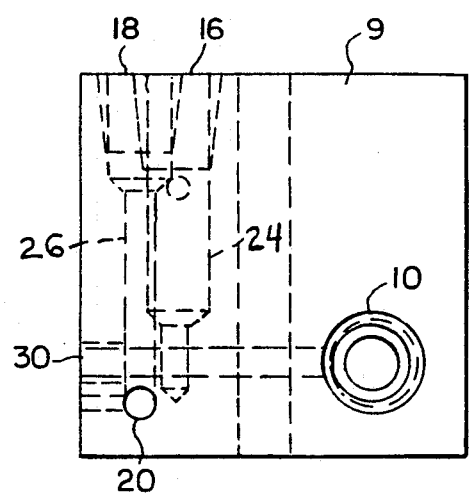
FIG. 3 is an end view of the block at the opposite end taken along section 3 of FIG. 1, and shown partly in cross-section.
Figure 4:
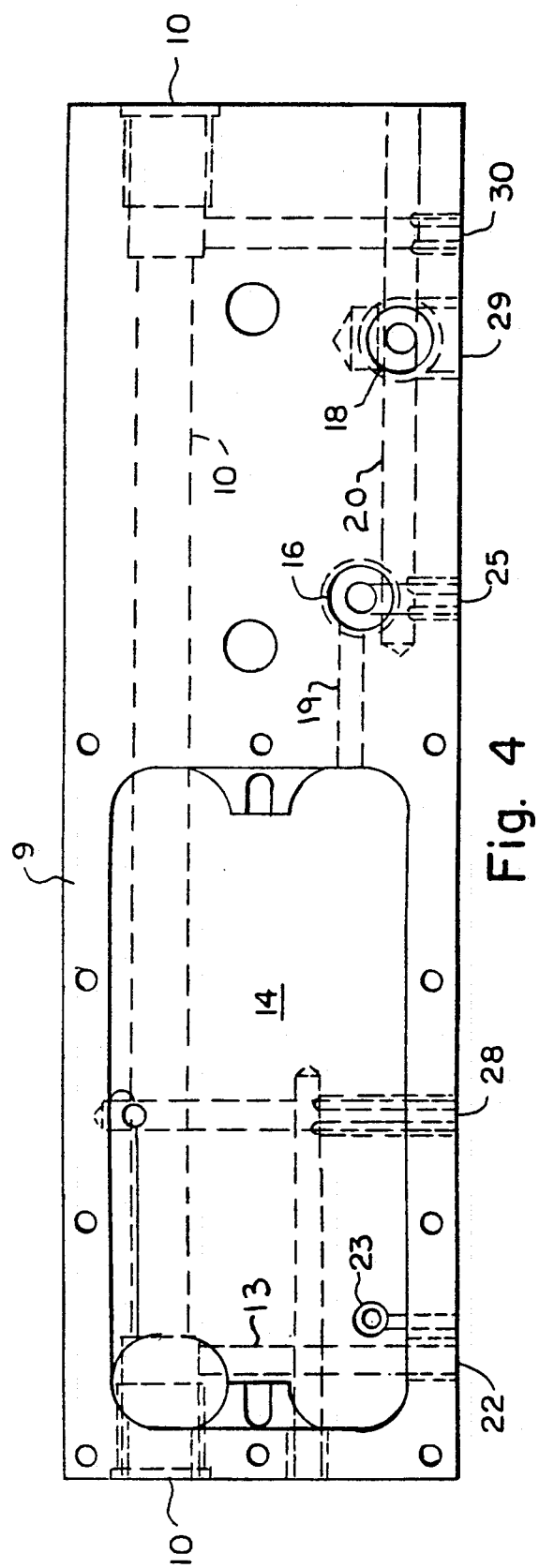
FIG. 4 is a top view of the block taken along section 4 of FIG. 1 and shown partly in cross-section.
Figure 5:
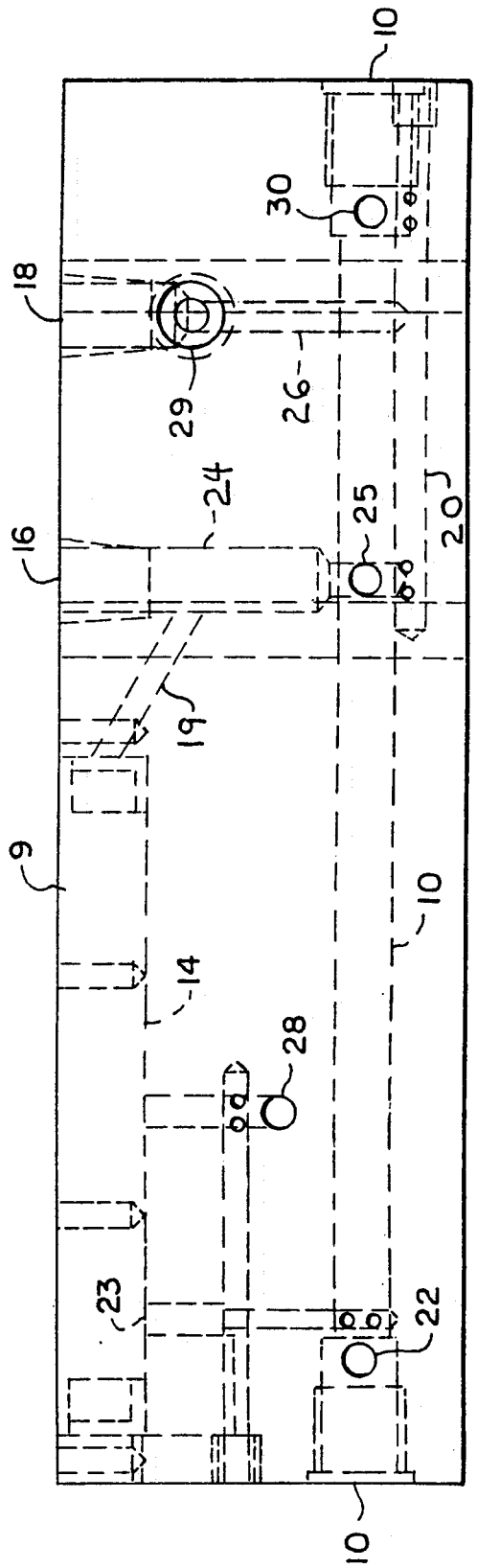
FIG. 5 is a side view of the block taken along section 5 of FIG. 1 and shown partly in cross-section; and, FIG. 6 is a flow diagram showing how the block of the invention is used in conjunction with valves, regulators and support equipment.
Figure 6:
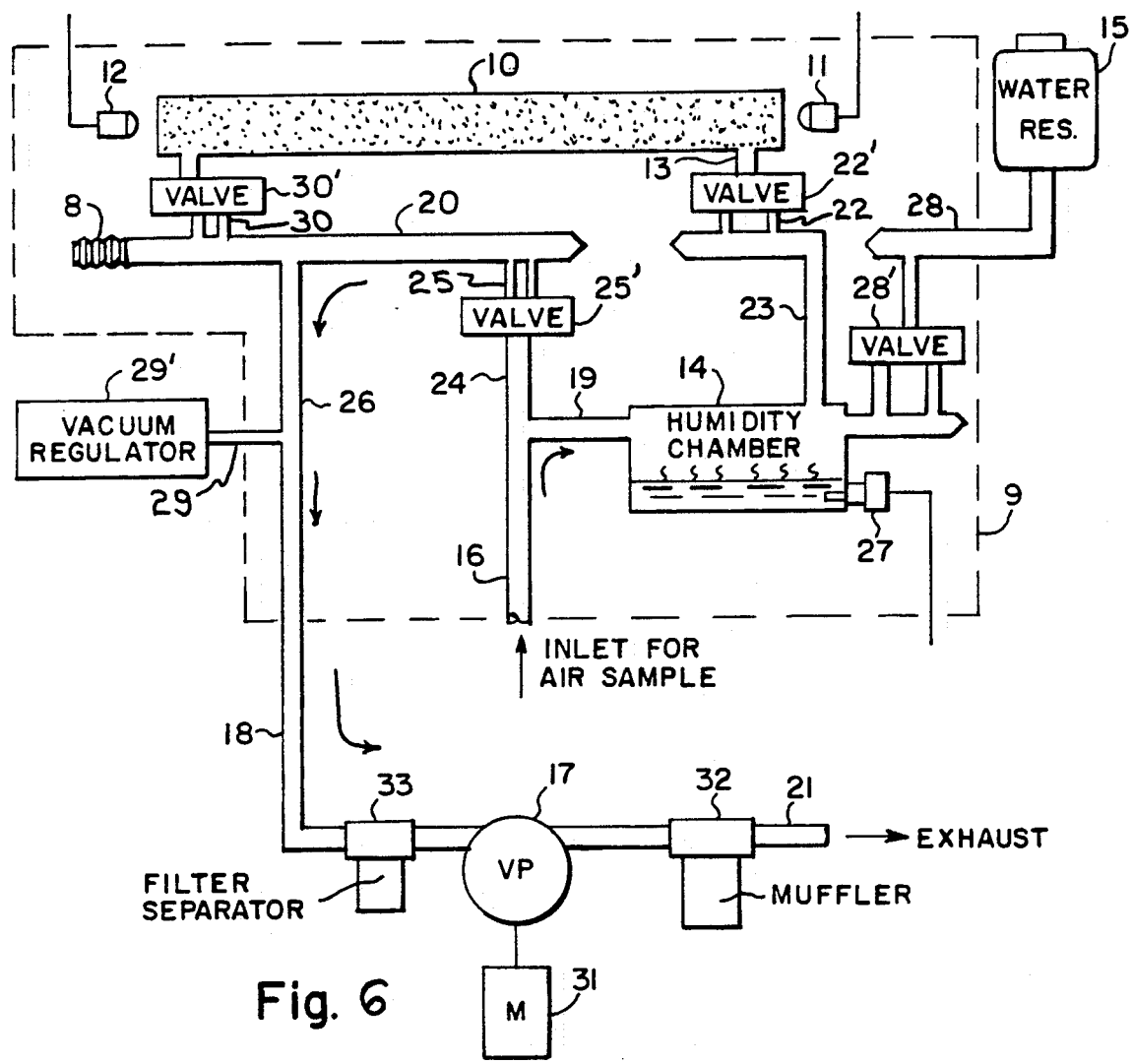

Referring to FIGS. 1-6 there is shown the block 9, according to the invention, having a humidity chamber 14 disposed in a portion of its top surface and shown as a troth. Within the humidity chamber is shown an opening 23 which connects to an opening 22 on the front surface thereof, and opening 28' which connects to opening 28 in the front surface of the block. Connected to opening 28 on the front surface is an external water reservoir is to supply water to humidity chamber 14. Opening 23, in the trough, allows the humidity developed within chamber 14 to travel to a cloud chamber 10 via a valve 22' connected in to opening 22 on the front of the block. The cloud chamber 10 consists of an elongated cylindrical hole that has been formed in the block throughout its entire length so that a photo transistor 12 and a source of illumination 11, such as an LED may be inserted at each end of the block. A vacuum valve 30' is connected through opening 30 which controls the flow of air at one end of cloud chamber 10. At the opposite end of cloud chamber 10, and connected through line 13 and into opening 22 on the front face of the block, is a humidity valve 22'. Humidity valve 22' also communicates through passageway 23 within the block to humidity chamber 14.

The top surface of the block 9 has an opening 16 which serves as an inlet opening for the air sample, and communicates through passageway 19 to humidity chamber 14, and to bypass valve opening 25 through passageway 24. In a similar manner, the bypass valve opening 25 is connected through passageway 20 to a vacuum valve opening 30.

Passageway 26 connects vacuum valve opening 30 to vacuum regulator opening 29 on the front face of the block. Passageway 26 is also connected to opening 18 on the top surface of the block, which serves as an exhaust exit for the gases that were originally fed in to the block through opening 16. As can be seen in detail in FIG. 6, the humidification and could chamber block 9, as shown in dotted line, serves also as a housing for vacuum valve 30', bypass valve 25', and humifidication valve 22' that are connected to openings 30, 25 and 22 respectively. In a similar manner, the vacuum regulator 29' can be connected to passageway 26 through opening 29. A water reservoir 15 can be connected through the humidification valve connected in opening 28. The exhaust opening 18 of the block is connectd to the series combination of a filter separator 33, a vacuum pump 17 driven by motor 31, a muffler 32, and an exhaust pipe 21. The Applicant incorporates by reference all of the specification of application 352,149 filed May 15, 1989 which describes the details of the operation of the particle concentration detector which uses block 9.

The block is preferably machined from the opaque plastic ertalyte. By combining all of the porting and passages, between the humidification chamber and the cloud chamber, all of the connecting passages have been minimized. Moreover, since the plastic material has insulating qualities, the block minimizes thermal gradients between the humidification chamber and the cloud chamber, thus eliminating the requirement of any thermal insulation that was formerly required in prior art devices using external interconnecting pipes or tubing. To the reliability of the particle concentration detector of application Ser. No. 352,149, has been greatly improved since the number of external, interconnecting pipes or tubing, has been greatly reduced. With the internal passagesways that have been machined in the block, leakly couplings from the prior art have been eliminated and the flow of gases travelling through these passageways, within the block, do not leak, nor can they be cross-connected due to the monolithic nature of the block of material. Many of the openings shown on the block are threaded, so that valves, photo detectors and input and output tubing, can be thread-ably secured to the block to form a compact particle concentration detection system.

While only a single embodiment has been shown and described, it is obvious that many changes and modifications may be made thereunto without departing from the spirit and scope of the claims.

What is claimed:

1. A device for determing the density or changes in density of small particles, comprising:
   a monolithic block of material that is impervious to light;
   an elongated chamber formed in said block and defining a cloud chamber for receiving a source of light at one end and a photo detector at the opposite end, said chamber having input and output passageways;
   a trough, formed in said block, and defining a humidification chamber;
   a first passageway for connecting said humidification chamber to the input passageway of said cloud chamber within said block;
   an air inlet passageway formed in said block;
   an intermediate passageway formed within said block and coupled to said air inlet passageway, said intermediate passageway being coupled with said humidity chamber and the output passageway of said cloud chamber; and,
   an exhaust opening formed in said block and communicative to said cloud chamber through the intermediate chamber for permitting a vacuum to be established in the intermediate passageway within said block, wherein said elongated chamber, intermediate passageway and trough are contained within said block to minimize the length of the connecting passageways.

2. The device as recited in claim 1, additionally comprising an opening formed in said block and disposed between said cloud chamber and the humidity chamber for receiving a humidity valve for regulating the humidity to the cloud chamber.

3. The device as recited in claim 1, additionally comprising a passageway disposed between one end of the cloud chamber and the exhaust opening to permit control of the vacuum in the cloud chamber.

4. The device as recited in claim 3, comprising a bypass valve opening disposed in the intermediate passageway between said humidity chamber and the exhaust opening to permit the closing off the passageway between the humidity chamber and the exhaust opening.

5. The device as recited in claim 4, comprising a vacuum regulator passageway disposed in the intermediate passageway between the exhaust opening at one end, and the bypass valve and vacuum valve openings at the other end within said block.

* * * * *